United States Patent
Lennartz et al.

(10) Patent No.: US 11,711,596 B2
(45) Date of Patent: Jul. 25, 2023

(54) SYSTEM AND METHODS FOR DETERMINING PROXIMITY RELATIVE TO AN ANATOMICAL STRUCTURE

(71) Applicant: Covidien LP, Mansfield, MA (US)

(72) Inventors: Amanda H. Lennartz, Erie, CO (US); Daniel A. Joseph, Golden, CO (US); Cornelia F. Twomey, Longmont, CO (US); Erin E. Wehrly, Longmont, CO (US); Pierre Gherardi, Longmont, CO (US); Tracy J. Pheneger, Longmont, CO (US); David M. Garrison, Longmont, CO (US); Tyler J. Bagrosky, Arvada, CO (US); Robert H. Wham, Boulder, CO (US); Jing Zhao, Superior, CO (US)

(73) Assignee: Covidien LP, Mansfield, MA (US)

( * ) Notice: Subject to any disclaimer, the term of this patent is extended or adjusted under 35 U.S.C. 154(b) by 39 days.

(21) Appl. No.: 17/111,348

(22) Filed: Dec. 3, 2020

(65) Prior Publication Data
US 2021/0234993 A1 Jul. 29, 2021

Related U.S. Application Data

(60) Provisional application No. 62/964,907, filed on Jan. 23, 2020.

(51) Int. Cl.
| | |
|---|---|
| *G06T 7/70* | (2017.01) |
| *H04N 23/50* | (2023.01) |
| *A61B 1/313* | (2006.01) |
| *A61B 1/05* | (2006.01) |
| *A61B 1/00* | (2006.01) |

(52) U.S. Cl.
CPC .......... *H04N 23/50* (2023.01); *A61B 1/00045* (2013.01); *A61B 1/05* (2013.01); *A61B 1/3132* (2013.01); *G06T 7/70* (2017.01); *G06T 2207/10068* (2013.01); *H04N 23/555* (2023.01)

(58) Field of Classification Search
CPC .... H04N 5/2251; G06T 7/70; A61B 1/00045; A61B 1/05; A61B 1/3132
See application file for complete search history.

(56) References Cited

U.S. PATENT DOCUMENTS

| | | |
|---|---|---|
| 4,543,959 A | 10/1985 | Sepponen |
| 5,800,350 A | 9/1998 | Coppleson et al. |
| 5,957,849 A | 9/1999 | Munro |
| 5,991,697 A | 11/1999 | Nelson et al. |
| 6,006,127 A | 12/1999 | Van Der Brug et al. |
| 6,109,268 A | 8/2000 | Thapliyal et al. |
| 6,241,725 B1 | 6/2001 | Cosman |
| 6,428,537 B1 | 8/2002 | Swanson et al. |

(Continued)

*Primary Examiner* — Hesham K Abouzahra
(74) *Attorney, Agent, or Firm* — Carter, DeLuca & Farrell LLP (57) ABSTRACT

A system includes a surgical instrument configured to perform a laparoscopic surgical operation, a location sensor configured to identify a spatial relationship between an anatomical structure and the surgical instrument, and a processor configured to receive a graphical representation of a patient, determine proximity of the distal end portion of the surgical instrument with the anatomical structure of the patient based on the spatial relationship, and generate a warning based on the determination of proximity.

17 Claims, 6 Drawing Sheets

(56) References Cited

U.S. PATENT DOCUMENTS

| | | |
|---|---|---|
| 6,546,270 B1 | 4/2003 | Goldin et al. |
| 6,569,098 B2 | 5/2003 | Kawchuk |
| 6,569,160 B1 | 5/2003 | Goldin et al. |
| 6,837,855 B1 | 1/2005 | Puech |
| 6,889,075 B2 | 5/2005 | Marchitto et al. |
| 7,089,045 B2 | 8/2006 | Fuimaono et al. |
| 7,099,712 B2 | 8/2006 | Fuimaono et al. |
| 7,155,270 B2 | 12/2006 | Solis et al. |
| 7,207,989 B2 | 4/2007 | Pike, Jr. et al. |
| 7,228,164 B2 | 6/2007 | Fuimaono et al. |
| 7,257,434 B2 | 8/2007 | Fuimaono et al. |
| 7,257,435 B2 | 8/2007 | Plaza |
| 7,302,285 B2 | 11/2007 | Fuimaono et al. |
| 7,615,015 B2 | 11/2009 | Coleman |
| 7,706,882 B2 | 4/2010 | Francischelli et al. |
| 7,819,860 B2 | 10/2010 | Wittenberger et al. |
| 7,917,312 B2 | 3/2011 | Wang et al. |
| 7,967,742 B2 | 6/2011 | Hoeg et al. |
| 8,183,745 B2 | 5/2012 | Trolier-McKinstry et al. |
| 8,617,155 B2 | 12/2013 | Johnson et al. |
| 9,375,196 B2 | 6/2016 | Zheng et al. |
| 9,730,672 B2 | 8/2017 | Zheng et al. |
| 2003/0045798 A1 | 3/2003 | Hular et al. |
| 2003/0120306 A1 | 6/2003 | Burbank et al. |
| 2004/0221853 A1 | 11/2004 | Miller |
| 2005/0027199 A1 | 2/2005 | Clarke |
| 2005/0143662 A1 | 6/2005 | Marchitto et al. |
| 2005/0217381 A1 | 10/2005 | Falk |
| 2006/0036162 A1 | 2/2006 | Shahidi et al. |
| 2006/0106375 A1 | 5/2006 | Werneth et al. |
| 2006/0184042 A1 | 8/2006 | Wang et al. |
| 2007/0106289 A1 | 5/2007 | O'Sullivan |
| 2007/0156128 A1 | 7/2007 | Jimenez |
| 2007/0167943 A1 | 7/2007 | Janssen et al. |
| 2007/0239007 A1 | 10/2007 | Silverman et al. |
| 2007/0248254 A1 | 10/2007 | Mysore Siddu et al. |
| 2008/0065178 A1 | 3/2008 | Kelleher et al. |
| 2009/0088634 A1 | 4/2009 | Zhao et al. |
| 2009/0163904 A1 | 6/2009 | Miller et al. |
| 2009/0216129 A1 | 8/2009 | Lasser et al. |
| 2009/0267773 A1 | 10/2009 | Markowitz et al. |
| 2009/0287223 A1 | 11/2009 | Pua et al. |
| 2009/0318756 A1 | 12/2009 | Fisher et al. |
| 2010/0023004 A1 | 1/2010 | Francischelli et al. |
| 2010/0217117 A1 | 8/2010 | Glossop et al. |
| 2011/0106052 A1 | 5/2011 | Chiang et al. |
| 2011/0230710 A1 | 9/2011 | Hoeg et al. |
| 2012/0010506 A1 | 1/2012 | Ullrich |
| 2012/0071757 A1 | 3/2012 | Salcudean et al. |
| 2012/0136242 A1 | 5/2012 | Qi et al. |
| 2013/0218024 A1 | 8/2013 | Boctor et al. |
| 2018/0140359 A1* | 5/2018 | Koyrakh ............... A61B 34/20 |
| 2019/0231220 A1* | 8/2019 | Refai .................... H04N 13/25 |

\* cited by examiner

SYSTEM AND METHODS FOR DETERMINING PROXIMITY RELATIVE TO AN ANATOMICAL STRUCTURE

CROSS-REFERENCE TO RELATED APPLICATIONS

This application claims the benefit of, and priority to, U.S. Provisional patent Application No. 62/964,907, filed on Jan. 23, 2020, the entire contents of which are hereby incorporated herein by reference.

FIELD

The present disclosure relates to surgical systems and methods for treating tissue. More particularly, the present disclosure relates to systems and methods for determining proximity of a surgical instrument relative to anatomical structures.

BACKGROUND

More and more surgeons are utilizing surgical robots, endoscopes, and endoscopic instruments that access organs through small puncture-like incisions in so-called laparoscopic surgical procedures. During laparoscopic procedures, however, poor visibility, lack of tactile response, confusion of the anatomy from patient to patient, and/or inadequate control of the instrumentation being utilized to perform the procedure may make such laparoscopic procedures more challenging.

SUMMARY

This disclosure generally relates to determination of proximity of a surgical instrument relative to an anatomical structure based on various sensor technologies so as to avoid inadvertent injuries to the anatomical structure.

Provided in accordance with aspects of the disclosure is a system for determining proximity of a surgical instrument with respect to an anatomical structure. The system includes a surgical instrument configured to perform a laparoscopic surgical operation, a location sensor configured to identify a spatial relationship between an anatomical structure and the surgical instrument, and a processor configured to receive a graphical representation of a patient, determine proximity of the distal end portion of the surgical instrument with the anatomical structure of the patient based on the spatial relationship, and generate a warning based on the determination of proximity.

In an aspect of the disclosure, the anatomical structure is a non-target anatomical structure.

In another aspect of the disclosure, the location sensor is further configured to emit a probing signal to the anatomical structure and to receive a signal reflected from the anatomical structure. The spatial relationship is a distance between the distal end portion and the anatomical structure based on the received signal.

In another aspect of the disclosure, the location sensor is a laparoscopic camera configured to capture an image of the surgical instrument and the anatomical structure. The processor identifies the spatial relationship based on the captured images.

In still another aspect of the disclosure, the processor is further configured to perform image processing on the captured image to determine the proximity of the distal end portion of the surgical instrument with the anatomical structure.

In yet another aspect of the disclosure, the processor determines the proximity based on a distance between the distal end portion and the anatomical structure.

In yet still another aspect of the disclosure, the graphical representation is a three-dimensional model or a live video.

Provided in accordance with aspects of the disclosure is a method for determining proximity of a surgical instrument with respect to an anatomical structure. The method includes providing a graphical representation of a patient, identifying a spatial relationship between an anatomical structure and a surgical instrument configured to perform a laparoscopic surgical operation, determining proximity of the distal end portion of the surgical instrument with the anatomical structure of the patient based on the spatial relationship, and generating a warning based on the determination of proximity.

In an aspect of the disclosure, the anatomical structure is a non-target anatomical structure.

In still another aspect of the disclosure, the method further includes emitting a probing signal to the anatomical structure, and receiving a signal reflected from the anatomical structure. The spatial relationship is a distance between the distal end portion and the anatomical structure based on the received signal.

In still another aspect of the disclosure, the method further includes capturing an image of the surgical instrument and the anatomical structure. The spatial relationship is based on the captured image.

In yet another aspect of the disclosure, the method further includes performing image processing on the captured image to determine the proximity of the distal end portion with the anatomical structure. The proximity is determined based on a distance between the distal end portion and the anatomical structure.

In yet still another aspect of the disclosure, the graphical representation is a three-dimensional model or a live video.

Provided in accordance with aspects of the disclosure is a nontransitory computer-readable storage medium storing a program for causing a computer to execute a method for determining proximity of a surgical instrument with respect to an anatomical structure. The method includes providing a graphical representation of a patient, identifying a spatial relationship between an anatomical structure and a surgical instrument configured to perform a laparoscopic surgical operation, determining proximity of the distal end portion of the surgical instrument with the anatomical structure of the patient based on the spatial relationship, and generating a warning based on the determination of proximity.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Surgical operations involve operations to target anatomical structures. Due to a limited view, poor visibility, lack of tactile response, confusion of the anatomy from patient to patient, and/or inadequate control of the instrumentation being utilized during surgical operations and, more specifically, laparoscopic surgical operations, it is advantageous to determine proximity of a surgical instrument with respect to non-target anatomical structures to avoid potential damage to these structures. Systems and methods in accordance with the present disclosure are provided for determining a distance between the surgical instrument and non-target anatomical structures and generating a warning when the distance is less than or equal to a predetermined threshold. Other aspects and features of the present disclosure are detailed below.

Figure 1:
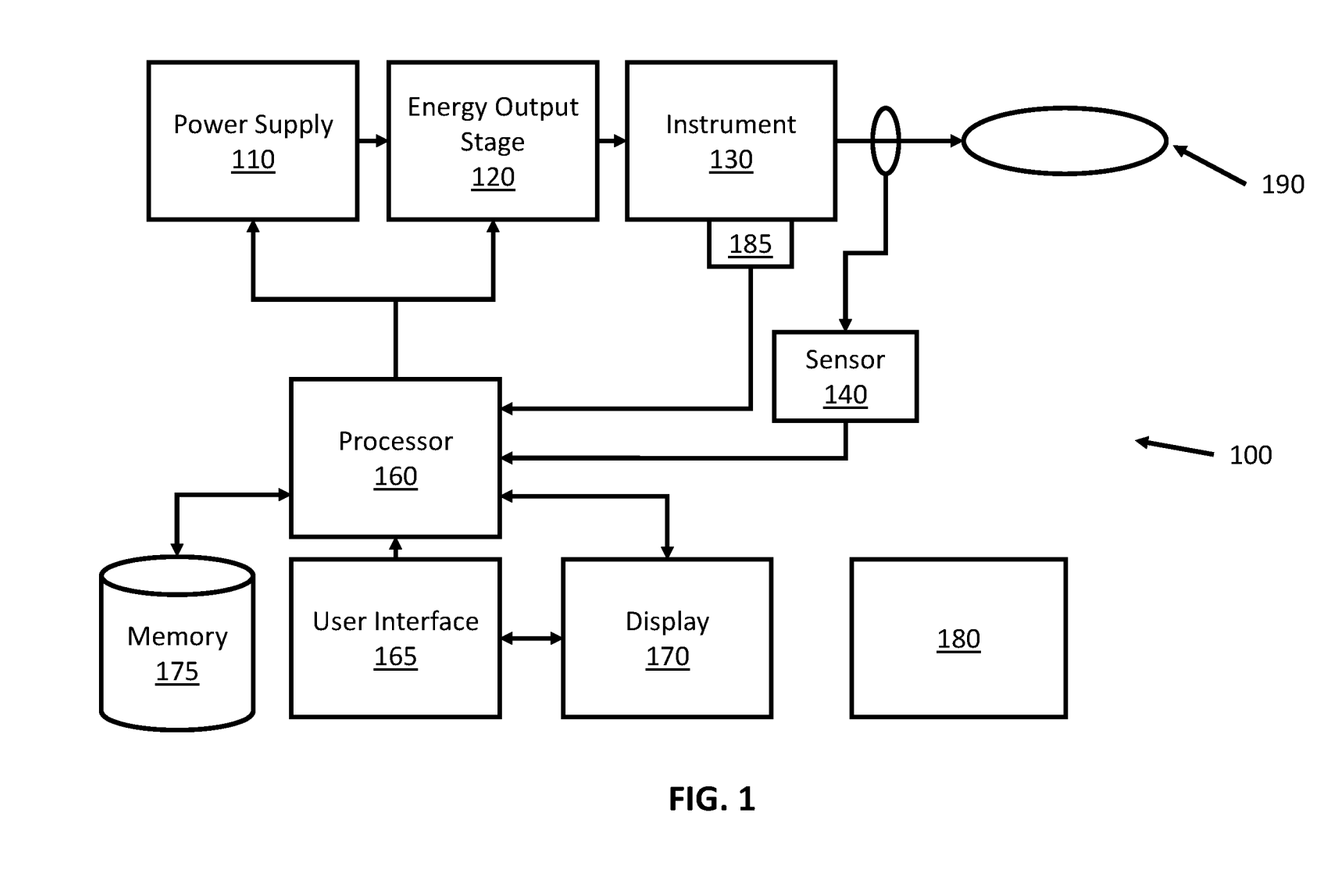
FIG. 1 is a schematic diagram of a surgical system in accordance with the present disclosure.

FIG. 1 shows a block diagram of a surgical system 100, which determines proximity of a surgical instrument 130 with respect to a non-target anatomical structure around a target anatomical structure, according to embodiments of the present disclosure. The surgical system 100 may use any type of energy to treat a target anatomical structure. The type of energy may include mechanical energy, acoustic energy, thermal energy, electrical energy, electromagnetic (EM) energy (e.g., optical energy or radio frequency (RF) energy), or ultrasonic energy. The surgical system 100 may use EM waves to determine a location of one or more elements of the surgical system 100 and synchronize the patient with a three-dimensional (3D) model of a patient. Further, the surgical system 100 may generate a warning that the non-target anatomical structure is in proximity to the surgical instrument 130. By doing the above, the surgical system 100 helps clinicians to perform surgical operations without unintentionally damaging the non-target anatomical structure (e.g., blood vessel, vile duct, gall bladder, lymph vessel, etc.).

In embodiments, the surgical system 100 may use EM waves to identify a location of one or more elements of the surgical system 100 and synchronize the patient with the 3D model. Further, the surgical system 100 may identify non-target anatomical structure, which can be critical to physiology of the patient, based on the 3D model, and warn the clinician when the non-target anatomical structure is in close proximity to the surgical instrument 130. By doing so, the surgical system 100 helps clinicians to perform surgical operations without unintentionally damaging the non-target anatomical structures.

In a case when the target anatomical structure and the non-target anatomical structure are a part of the same organ (e.g., an entrapped intestine along the intestine), the target and non-target structures are close to each other. In this case, close proximity may be determined based on the distances from the target and non-target anatomical structures.

Prior to or concurrently with surgical operations, a three-dimensional (3D) model is generated to visually display patient's anatomy. During an imaging/planning stage, a computer utilizes computed tomography (CT) image data or other image data in the Digital Imaging and Communications in Medicine (DICOM) format, for generating and viewing a 3D model of the patient's body. In embodiments, the 3D model may be generated in real time based on a live video. The 3D model and image data derived from the 3D model enables identification of the region of interest (automatically, semi-automatically or manually), and allows for selection of a pathway to the region of interest. More specifically, the CT scans are processed and assembled into a 3D volume, which is then utilized to generate the 3D model of the patient's body. The surgical system 100 may include a memory 175 to store the 3D model or receive the 3D model from another computer, which has generated or stored the 3D model. The surgical system 100 may be coupled to a display 170 and cause the display 170 to display the 3D model on its screen.

The surgical system 100 may include a power supply 110, an energy output stage 120, and the surgical instrument 130. The power supply 110 supplies power to the energy output stage 120, which generates energy and provides the energy to the surgical instrument 130. The surgical instrument 130, in turn, applies the generated energy to the target anatomical structure 190. For an RF-based tissue-sealing system, the energy output stage 120 generates RF energy and the surgical instrument 130 applies the RF energy to the target anatomical structure 190 through at least one contact to treat the target anatomical structure 190. Various other types of instruments 130 may be encompassed in this disclosure as understood by a person having ordinary skill in the art.

The surgical system 100 may also include a sensor 140, a processor 160, a user interface 165, and display 170. The sensor 140 senses various parameters and/or properties of the RF energy applied by the surgical instrument 130 at the operating site and transmits sensor signals representing the sensed parameters or properties of the RF energy to the processor 160. The processor 160 processes the sensor signals and generates control signals based on the processed sensor signals to control the power supply 110 and/or the energy output stage 120. For example, the processor 160 may regulate the voltage or current output from the power supply 110 or the energy output stage 120 based on the processed sensor signals.

The sensor 140 is configured to measure various electrical or electromechanical conditions at the operating site such as impedance, changes in the impedance, temperature, changes in the temperature, leakage current, applied voltage, and applied current at the target anatomical structure. The sensor 140 continuously measures one or more of these conditions so that the processor 160 can continually adjust the energy output from the power supply 110 and/or the energy output stage 120 during a surgical operation. For example, in an RF-based vessel sealing, the sensor 140 may measure the impedance and the processor 160 may adjust the voltage generated by the energy output stage 120.

The user interface 165 is coupled to the processor 160 allowing a user to control various parameters of the energy applied to the target anatomical structure 190 during a surgical procedure. For example, the user interface 165 may allow a user to manually set, regulate and/or control one or more parameters of the energy delivered to the target anatomical structure 190, such as voltage, current, power, frequency, and/or pulse parameters, e.g., pulse width, duty cycle, crest factor, and/or repetition rate.

The processor 160 may be designed to execute software instructions, which are saved in the memory 175, for processing data received from the user interface 165 and for outputting control signals to the power supply 110 and/or the energy output stage 120. The software instructions may be uploaded to or stored in an internal memory of the processor 160, an internal or external memory bank accessible by the processor 160 and/or an external memory, e.g., an external hard drive, floppy diskette, or CD-ROM. Control signals generated by the processor 160 may be converted to analog signals by a digital-to-analog converter (DAC) (not shown) before being applied to the power supply 110 and/or energy output stage 120.

For embodiments of an RF-based tissue-sealing system, the power supply 110 is a high-voltage DC power supply that produces RF current. In these embodiments, the processor 160 transmits control signals to the power supply to control the magnitudes of the RF voltage and current output from the power supply 110. The energy output stage 120 receives the RF current and generates one or more pulses of RF energy. The processor 160 generates control signals to regulate the pulse parameters of the RF energy, such as pulse width, duty cycle, crest factor, and repetition rate. In other embodiments, the power supply 110 is an AC power supply, and the energy output stage 120 may vary the waveform of the AC signal generated by the power supply 110 to achieve a desired waveform.

As described above, the user interface 165 may include an input device, such as a keyboard or touch screen, through which a user enters data and commands. The data may include the type of instrument, the type of procedure, and/or the type of the target anatomical structure. The commands may include target effective voltage, current, or power level, or other commands for controlling parameters of the energy that is delivered from the energy output stage 120 to the surgical instrument 130.

In embodiments, the user interface 165 may be incorporated into the display 170. For example, the display 170 may be touch sensitive and display graphical controls (e.g., a slider, radio button, check box, input box, etc.) to adjust various parameters. In such configurations, a clinician adjusts values of the various parameters by touching/holding/dragging the graphical controls on the display 170.

The surgical system 100 may include an EM wave generator 180 and an EM sensor 185. When a patient is placed on a surgical table for receiving a surgical operation, an EM wave is generated by the EM wave generator 180. The generated EM wave surrounds the patient. The EM sensor 185, which may be installed/fixed on the surgical instrument 130 a predetermined distance from its distal tip or other point of reference, senses the strength of the EM wave at the position of the surgical instrument 130. Based on the strength of the EM wave, the processor 160 is able to estimate a location of the surgical instrument 130 with respect to an origin of the EM coordinate system. The EM sensor 185 may be installed on another element of the surgical system 100 to monitor the spatial relationship within the surgical system 100. The EM navigation may be guided based on a time of arrival at the target anatomical structure or other landmark anatomical structures.

In embodiments, the processor 160 may synchronize the EM coordinate system with the coordinate system of the 3D model. A graphical representation of the surgical instrument 130 may be displayed at the corresponding location in the 3D model in an augmented way on the screen of the display 170. Thus, when the 3D model is moved or rotated, the graphical representation of the surgical instrument 130 is correspondingly moved or rotated.

Based on the 3D model, the surgical system 100 may identify the target anatomical structure 190 and non-target anatomical structure around the target anatomical structure 190. The estimated location of the surgical instrument 130 is used to determine whether the non-target anatomical structure is in proximity to respect to the surgical instrument 130.

In an alternative embodiment, the reference numeral 180 may be an endoscope, which may generate a live video when the endoscope 180 is entered and navigated toward the target anatomical structure 190, and the reference numeral 185 may be a probe, which may emit a probing signal toward the non-target anatomical structures around the target anatomical structure 190. Based on the received signal and the live video, the surgical system 100 may identify critical structures among the non-target anatomical structures. The probe signal is reflected from the non-target anatomical structures and the reflected signal is received by the probe 185. The surgical system 100 then determines proximity of the surgical instrument 130 with respect to the non-target anatomical structures, which may be critical to physiology of the patient.

Further, the probe 185 may also emit a probing signal to and receive the signal reflected from the surgical instrument 130. Thus, based on the live video and the distances from the probe 185 to the surgical instrument 130 and the non-target anatomical structure, the distance between the non-target anatomical structure and the surgical instrument 130 may be calculated.

In embodiments, the processor 160 of the surgical system 100 may estimate a distance between the surgical instrument 130 and the non-target anatomical structure and generate a warning when the distance between the surgical instrument 130 and the non-target anatomical structure is less than or equal to a predetermined distance. The predetermined distance is a threshold indicating that the surgical instrument 130 may hit or touch the non-target anatomical structure with a small movement of the surgical instrument 130. The warning may be audible sounds, haptic vibrations, flashing lights, or any suitable means that brings attention of clinicians.

In embodiments, the processor 160 may estimate a speed of the surgical instrument 130 toward the target anatomical structure and generate a warning when the speed is too fast toward the anatomical structure. The processor 160 may record times of navigation toward the target anatomical structure and the surgical operations to the target anatomical structure so that chronology of the surgery is recorded with timestamps. Such record may also be recorded with the live view video or any audios. A warning may be generated when a level of risk or hazard is over a threshold level based on these records.

In embodiments, the surgical system 100 may be a robotic surgical system, which may be able to automatically determine a distance between the surgical instrument 130 and the non-target anatomical structure and generate a warning when the distance is less than or equal to the predetermined distance. The robotic surgical system may halt or stop surgical operations to avoid potential damages to the patient.

In embodiments, the surgical instrument 130 may include a 3D camera or other sensor (e.g., a laser light sensor, optical light sensor), which is capable of sensing a distance. For example, the 3D camera may determine the distance based on stereoscopic images and the laser light sensor may determine the distance based on the reception time and the emitting time.

Figure 2:
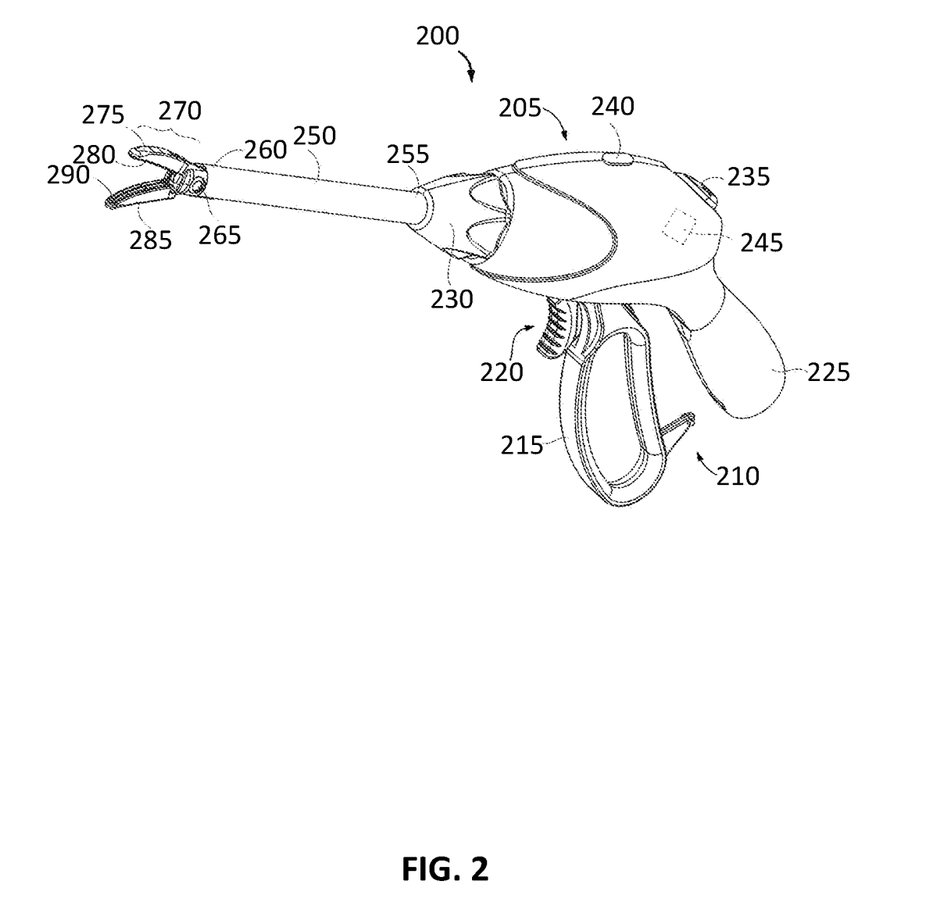
FIG. 2 is a perspective view of an energy-delivery device including an end effector assembly in accordance with the present disclosure.

FIG. 2 shows an energy-delivery forceps 200, as an example of the surgical instrument 130 of FIG. 1, for treating a target anatomical structure according to embodiments of the present disclosure. The energy-delivery forceps 200 includes a housing 205, a handle assembly 210, a trigger assembly 230, a rotatable assembly 230, and the end effector assembly 270. The end effector assembly 270 may include any feature or combination of features of jaw members. One or more components of the energy-delivery forceps 200, e.g., the housing 205, the rotatable assembly 230, and/or the end effector assembly 270, may be adapted to mutually cooperate to grasp, seal, divide and/or sense a target anatomical structure, e.g., tubular vessels and vascular tissue. In some embodiments, the trigger assembly 230 may be configured to actuate a cutting function of the energy-delivery forceps 200 or to actuate another component, as described below.

The end effector assembly 270 generally includes two jaw members 275 and 285 disposed in opposing relation relative to one another. One or both of the jaw members 275 and 285 are movable from a first position wherein the jaw members 275 and 285 are disposed in spaced relation relative to one another to a second position wherein the jaw members 275 and 285 cooperate to grasp tissue therebetween.

The energy-delivery forceps 200 includes an elongated shaft 250 having a distal portion 260 configured to mechanically engage the end effector assembly 270. The proximal end 255 of the shaft 250 is received within the housing 205. The rotatable assembly 230 is mechanically associated with the shaft 250 such that rotational movement of rotatable assembly 230 imparts similar rotational movements to the shaft 250 that, in turn, rotates the end effector assembly 270.

The handle assembly 210 includes a fixed handle 225 and a movable handle 215. In some embodiments, the fixed handle 225 is integrally associated with the housing 205, and the movable handle 215 is selectively movable relative to the fixed handle 225. The movable handle 215 of the handle assembly 210 is ultimately connected to a drive assembly. As can be appreciated, applying force to move the movable handle 215 toward the fixed handle 225 moves a drive sleeve through the shaft 250 to impart movement to the jaw members 275 and 285 from an open position, wherein the jaw members 275 and 285 are disposed in spaced relation relative to one another, to a clamping or closed position, where the jaw members 275 and 285 cooperate to grasp tissue located therebetween.

In some embodiments, the end effector assembly 270 may be configured as a unilateral assembly that includes a stationary jaw member mounted in fixed relation to the shaft 250 and a pivoting jaw member movably mounted about a pin 265. Alternatively, the energy-delivery forceps 200 may include a bilateral assembly, i.e., both jaw members 275 and 285 move relative to one another. The jaw members 275 and 285 may be curved at various angles to facilitate manipulation of tissue and/or to provide enhanced line-of-sight for accessing targeted tissues.

The first and second switch assemblies 235 and 240 are configured to selectively provide energy to the end effector assembly 270. More particularly, the first switch assembly 235 may be configured to perform a first type of surgical procedure (e.g., seal, cut, and/or sense) and a second switch assembly 240 may be configured to perform a second type of surgical procedure (e.g., seal, cut, and/or sense). It should be noted that the presently-disclosed embodiments may include any number of suitable switch assemblies and are not limited to the switch assemblies 235 and 240. It should further be noted that the presently-disclosed embodiments may be configured to perform any suitable surgical procedure and are not limited to only sealing, cutting and sensing.

The energy-delivery forceps 200 may include a controller 245. In some embodiments, the controller 245 may be provided as a separate component coupled to the energy-delivery forceps 200 or integrated within the energy-delivery forceps 200. The controller 245 may include any type of computing device, computational circuit, or any type of processor or processing circuit capable of executing a series of instructions that are stored in a memory. The controller 245 may be configured to control one or more operating parameters associated with an energy source (e.g., the power supply 100 or the energy output stage 120 of FIG. 1) based on one or more signals indicative of user input, such as generated by the first and second switch assemblies 235 and 240 and/or one or more separate, user-actuatable buttons or switches. Examples of switch configurations that may be suitable for use with the energy-delivery forceps 200 include, but are not limited to, pushbutton, toggle, rocker, tactile, snap, rotary, slide and thumbwheel. In some embodiments, the energy-delivery forceps 200 may be selectively used in either a monopolar mode or a bipolar mode by engagement of the appropriate switch.

The first and second switch assemblies 235 and 240 may also cooperate with the controller 245, which may be configured to automatically trigger one of the switches to change between a first mode (e.g., sealing mode) and a second mode (e.g., cutting mode) upon the detection of one or more parameters or thresholds. In some embodiments, the controller 245 is configured to receive feedback information, including various sensor feedback with regard to temperature of tissue, electrical impedance of tissue, jaw closure pressure, jaw positioning, and/or other various feedback information, e.g., using Raman spectroscopy, laser speckle imaging, optical imaging, fluorescence spectroscopy, and/or laser-induced tissue fluorescence, and to control the energy source based on the feedback information.

Embodiments of the present disclosure allow the jaw members 275 and 285 to seal and/or cut the target anatomical structure. The controller 245 may include a feedback loop that indicates when a surgical operation is complete based upon one or more of the following parameters: temperature, change in impedance of the target anatomical structure over time and/or changes in the optical or electrical power or current applied to the target anatomical structure over time, rate of change of these properties and combinations thereof. An audible or visual feedback monitor may be employed to convey information to the surgeon regarding the overall quality and/or the completion of the surgical operation over the target anatomical structure.

In embodiments, an endoscope may be integrated with the energy-delivery forceps 200 so that a live video may be oriented or rotated along movements of the energy-delivery forceps 200. Further, a probe may also be integrated with the energy-delivery forceps 200, in particular, at the two jaw members 275 and 285. Thus, the distance calculated based on the probing and reflected signals from non-target anatomical structures, which may be critical, can be used to estimate a distance between the energy-delivery forceps 200 and the non-target anatomical structures based on spatial relationship between the distal tip of the energy-delivery forceps 200 and the probe.

Figure 3:
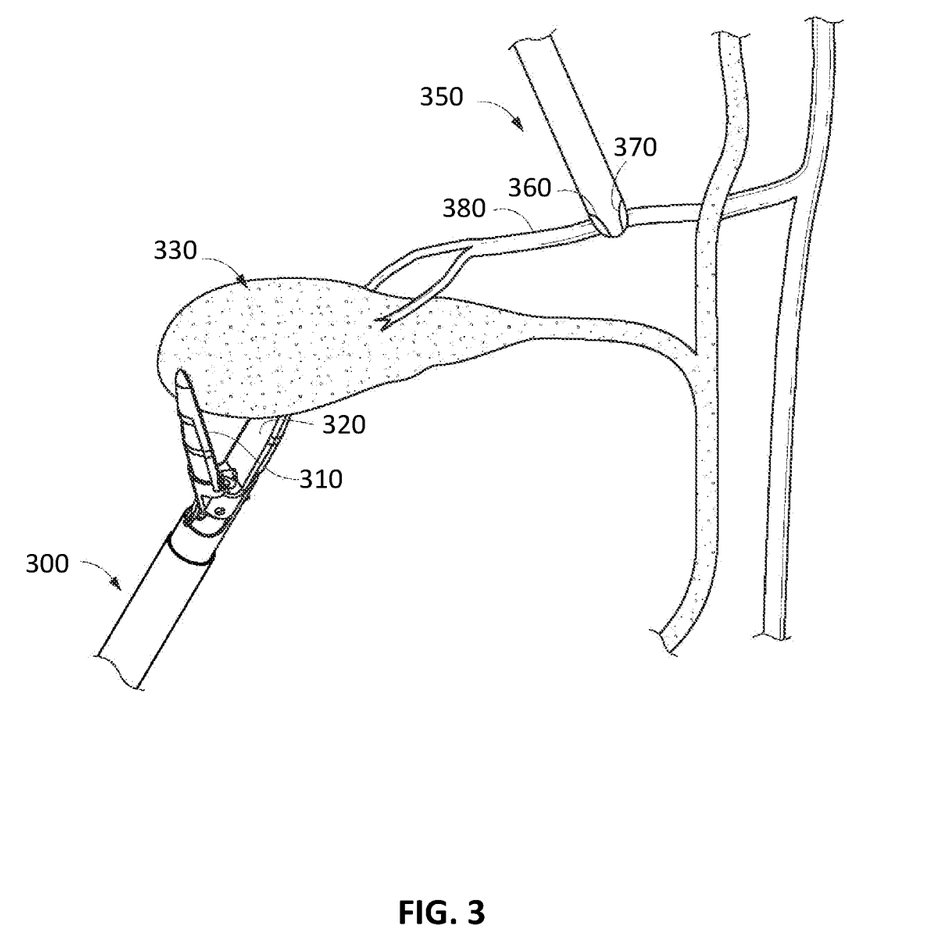
FIG. 3 is a perspective view of another energy-delivery device disposed relative to an anatomical structure (e.g., gallbladder) of a patient in accordance with the present disclosure.

FIG. 3 shows an end effector 300 of another surgical instrument, which may be used during a surgical operation in conjunction with a probe 350 to transmit response signals reflected from anatomical structures such that the processor 160 of FIG. 1 may calculate a signature property measurement of the anatomical structures to identify whether or not the anatomical structure is a target. More specifically, the end effector 300 is shown in an open position with a target anatomical structure 330 (e.g., gallbladder) disposed between the transmitting and receiving electrodes 310 and 320. The probe 350 is positioned about an anatomical structure (e.g., common bile duct) near the target anatomical structure 330. In this scenario, prior to grasping the target anatomical structure 330 with the end effector 300, the probe 350 may be positioned around the target anatomical structure 330 to determine whether or not the end effector 300 is near the target anatomical structure.

The probe 350 may include a transmitting probe portion 360 and a receiving probe portion 370. The transmitting probe portion 370 transmits a probing signal to anatomical structures located near the target structure 330 and the receiving probe portion 370 receives the probing signal reflected from the anatomical structures. The processor of the surgical system processes the reflected probing signals to identify the target anatomical structure 330. When the end effector 300 is moved to the target anatomical structure 330 to perform a surgical operation to the target anatomical structure 330, the transmitting probe portion 370 may transmit the probing signal to anatomical structures located near the target structure 330 and the probing signal received by the receiving probe portion 370 may be processed to determine whether the non-target anatomical structure is close to the end effector 300. In a case when a non-target anatomical structure is an anatomical structure and is sufficiently near the end effector 300, a warning may be generated to give a notice to a surgeon of proximity of the non-target anatomical structure, which may be critical to physiology of the patient, with respect to the target anatomical structure 330.

In embodiments, the probe 350 may be incorporated into the end effector 300. For example, the transmitting probe portion 360 and the receiving probe portion 370 may be incorporated into one or both of the transmitting and receiving electrodes 310 and 320. Hence, when the end effector 300 is moving or rotating, the surgeon may be informed along the movements of the end effector 300 that a non-target anatomical structure 380 is close to the end effector 300. For example, as shown in FIG. 3, the target anatomical structure 330 is a gallbladder and the other anatomical structures are non-targets. The end effector 300 may further include the features of and be configured similar to the end effector 270 of the forceps 100 (FIG. 2) or may be configured as any other suitable end effector.

The probing signal and the reflected signal may be used to determine whether or not a non-target anatomical structure is critical to physiology of the patient. When a 3D model is used, anatomical structures, which are critical, may be identified in consideration of the surgical operation prior to navigation to the target anatomical structure 330. When a live view is used, anatomical structures may be identified and indicated on a display displaying the live view, e.g., overlaid onto the display, or projected into the surgeon's field of view, e.g., using augmented reality. Further, the distance may be also calculated based on the probing signal and the reflected signal.

When the end effector 300 is close to the target anatomical structure 330, there is no warning. Further, when the end effector 300 is close to a non-target non-critical anatomical structure, there is no warning. However, when the end effector 300 is close to the non-target anatomical structure 380, which may be critical structure (e.g., a common bile duct), a warning may be generated to the surgeon.

Figure 4:
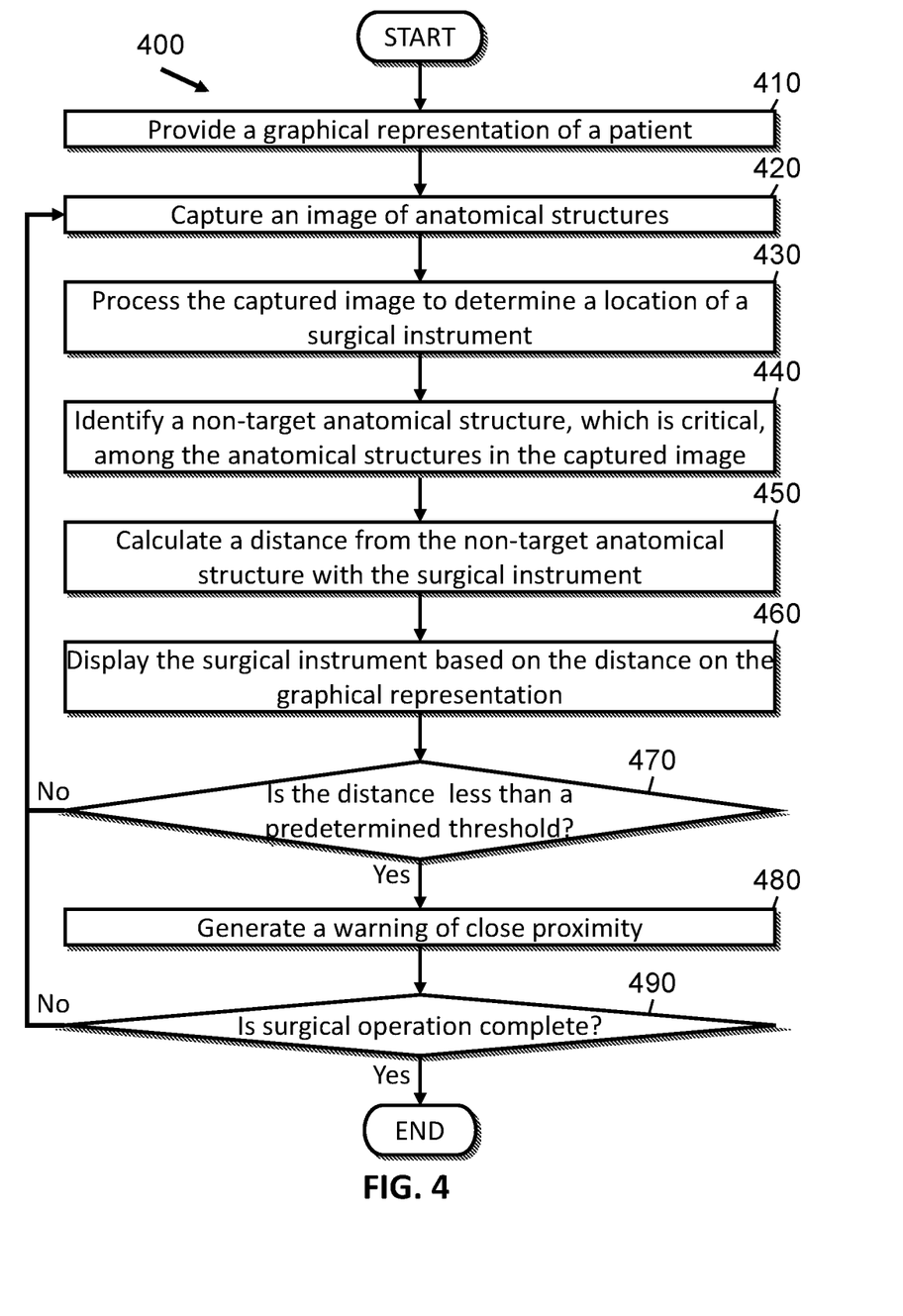
FIGS. 4 and 5 are flowcharts illustrating methods for determining proximity of a surgical instrument with respect to an anatomical structure according to the present disclosure.

FIG. 4 shows a flowchart illustrating a method 400 for determining proximity of a surgical instrument with respect to a non-target anatomical structure according to embodiments of the present disclosure. The method 400 provides a graphical representation, e.g., a 3D model or a video, of a patient to a surgical system in step 410. Where the graphical representation is a 3D model, the 3D model may include a target anatomical structure in the patient based on CT image data or other image data in the DICOM format. The 3D model, or other graphical representation, may also include anatomical structures, which are critical and non-critical, other than the target anatomical structure. The 3D model, or other graphical representation, may be used to identify which anatomical structure is critical or non-critical.

The surgical system may include EM tracking sensors fixedly or slidably installed on an end effector having two jaw members. Further, the surgical system may include an endoscope, which captures one or more images of anatomical structures while approaching toward the target anatomical structure in step 420. The captured anatomical structures may include the target anatomical structure, non-target anatomical structures, which are critical, and non-target anatomical structures, which are not critical, and the surgical instrument.

In step 430, the surgical system processes the captured image to determine a location of the surgical instrument in real time with respect to surrounding anatomical structures in the surgical site. The location of the surgical instrument may also be determined based on the EM tracking sensor installed on the surgical instrument. The location determined by the EM tracking sensor may identify a position within the graphical representation. Thus, the location determined by the captured image may be synchronized with the location determined by the EM tracking sensor.

In an aspect, a scale factor may be used in synchronization of the locations. The scale factor may be a ratio between the dimension in the real space and the dimension in the graphical representation. Thus, based on the scale factor, the spatial relationship between the surgical instrument and the non-target anatomical structure can be calculated.

While the captured image is processed in step 430, surrounding anatomical structures in the captured image may be identified. In step 440, among the identified anatomical structures, a non-target anatomical structure may be identified. For example, non-target anatomical structures may include a blood vessel, vile duct, gall bladder, lymph vessel, and other internal organs (e.g., gallbladder, kidney, spleen, lung, heart, etc.). This list is an exemplary purpose only and can be extended in consideration of the surgical operation.

While the surgical instrument is navigating toward the target anatomical structure, the clinician may be able to minimize any harmful contacts with non-target anatomical structures.

When the surgical instrument arrives near the target anatomical structure, the surgical system may calculate a distance between the surgical instrument and any non-target anatomical structures in step 450.

Since the clinician may have a limited view during the surgical operation, it is beneficial to showing the spatial relationship between the surgical instrument and the non-target anatomical structures. A second graphical representation of the surgical instrument may be display over first graphical representation, e.g., the 3D model, with respect to the non-target anatomical structure on a display screen based on the calculated distance in step 460. The target anatomical structure may also be displayed with respect to the non-target anatomical structure and the graphical representation of the surgical instrument.

In step 470, it is determined whether or not the distance between the surgical instrument and the non-target anatomical structure is less than or equal to a predetermined threshold. The predetermined threshold is a value indicating a potential harm to the non-target anatomical structure with a high probability.

In a case where the distance is determined not to be less than or equal to the predetermined threshold in step 470, the method 400 keeps performing steps 420-470 until the distance is determined to be less than or equal to the predetermined threshold.

When it is determined that the distance is less than or equal to the predetermined threshold, the surgical system may generate a warning of close proximity to the clinician in step 480. The warning may be audible sounds, haptic vibrations to any input device which the clinician is holding, flashing lights on the display screen, or any suitable warning that brings the clinician's attention.

In an embodiment, when it is determined that the distance is much less than the predetermined threshold, thus indicating a high probability of causing damages to the non-target anatomical structure, the warning may cause the surgical system in a pending state so as to stop delivering energy or even to stop the whole system, without an appropriate surgeon's overriding command.

The surgical operation is performed on the target anatomical structure and it is determined whether or not the surgical operation is complete in step 490. When it is not complete, the method 400 continues to perform steps 420-490.

When it is determined that the surgical operation is complete in step 490, the method 400 is likewise complete.

In an embodiment, after the surgical operation is complete, steps 420-480 may be performed while the clinician withdraws the surgical instrument from the target anatomical structure so as to minimize potentially harmful contacts with non-target anatomical structures.

Figure 5:
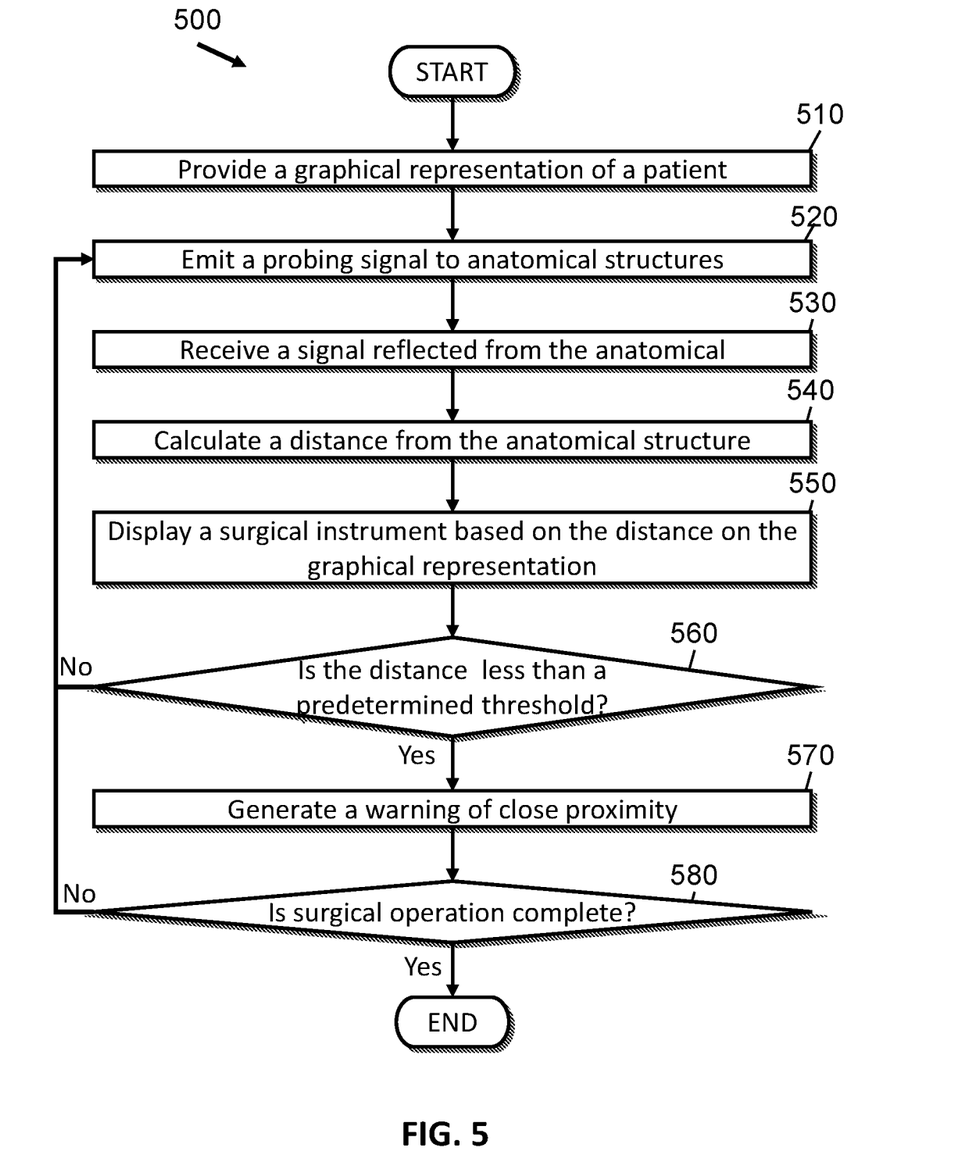

FIG. 5 shows a flowchart illustrating a method 500 for determining proximity of a surgical instrument with respect to a non-target anatomical structure according to embodiments of the present disclosure. The method 500 provides a graphical representation, e.g., a 3D model or a video, of a patient to a surgical system in step 510. Where the graphical representation is a 3D model, the 3D model, or other graphical representation, may include a target anatomical structure in the patient based on CT image data or other image data in the DICOM format. The 3D model, or other graphical representation, may also include anatomical structures, which are critical and non-critical, other than the target anatomical structure. The surgical system may display the target anatomical structure and non-target anatomical structures in different colors or in a way so that the clinician may be able to differentiate them from each other.

The surgical system may include EM tracking sensors fixedly or slidably installed on an end effector of the surgical instrument. Further, the surgical system may include a probe, which also includes an EM tracking sensor.

Based on the graphical representation, the clinician may position a probe toward a non-target anatomical structure. In step 520, the probe may emit a probing signal to surrounding anatomical structures while navigating toward the target anatomical structure, and in step 530, the probe may receive a signal reflected from the surrounding anatomical structures.

Based on the reflected signal, the surgical system may calculate a distance from the surrounding anatomical structures from the probe in step 540. In particular, a distance from a non-target anatomical structure may be calculated. Further, based on the EM tracking sensor installed on the probe, the location of the probe may be identified with respect to the coordinate system of the 3D model or other graphical representation. The distance between the surgical instrument and the non-target anatomical structure may be calculated from the distance between the probe and the non-target anatomical structure and the location of the surgical instrument.

In an aspect, the probe may be integrated with the surgical instrument. Thus, there is one EM tracking sensor for the surgical instrument and the probe. Based on the predetermined distance with respect to the EM tracking sensor from the end portion of the surgical instrument and the probe, the locations of the probe and the surgical instrument can be identified. Further, based on the EM tracking sensor installed on the surgical instrument, the location of the surgical instrument may be identified with respect to the coordinate system of the 3D model or other graphical representation. The surgical system may display the surgical instrument and the non-target anatomical structure based on identified locations of the surgical instrument and the probe.

In step 550, the surgical system may display the non-target anatomical structure with respect to the surgical instrument. In this way, the clinician can see the spatial relationship between them even with a limited view.

In step 560, it is determined whether or not the distance between the surgical instrument and the non-target anatomical structure is less than or equal to a predetermined threshold. The predetermined threshold is a value indicating a potential harm to the non-target anatomical structure with a high probability.

In a case where the distance is determined not be less than or equal to the predetermined threshold in step 560, the method 500 keep performing steps 520-560 until the distance is determined to be less than or equal to the predetermined threshold.

When it is determined that the distance is less than or equal to the predetermined threshold, the surgical system may generate a warning of close proximity to the clinician in step 570. The warning may be audible sounds, haptic vibrations to any input device which the clinician is holding, flashing lights on the display screen, or any suitable warning that brings the clinician's attention.

The surgical operation is performed on the target anatomical structure and it is determined whether or not the surgical operation is complete in step 580. When it is not complete, the method 500 keep performing steps 520-580.

When it is determined that the surgical operation is complete in step 580, the method 500 is likewise complete.

In an embodiment, after the surgical operation is complete, steps 520-570 may be performed while the clinician withdraws the surgical instrument from the target anatomical structure so as to minimize potentially harmful contacts with non-target anatomical structures.

Figure 6:
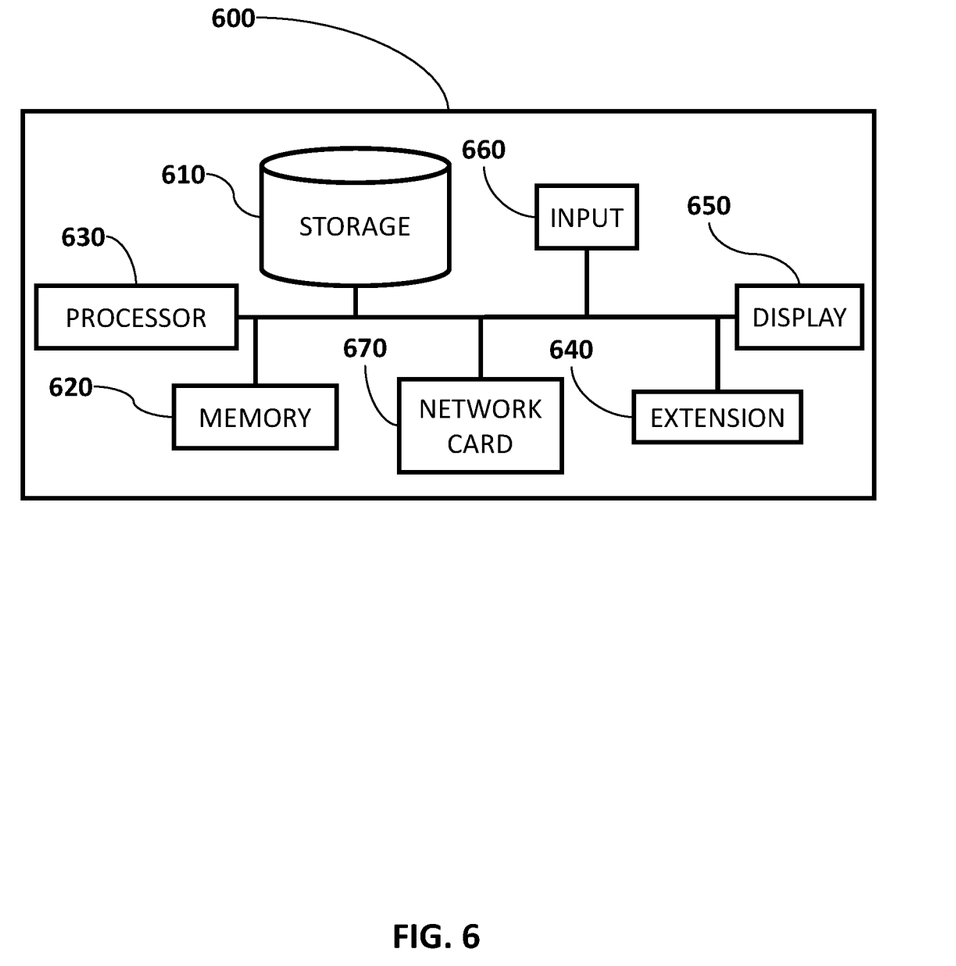
FIG. 6 is a block diagram of a computing device according to the present disclosure.

FIG. 6 is a block diagram for a computing device 600 representative of combination of the processor 160, the display 170, the user interface 165, and the memory 175 of FIG. 1 or the controller 245 of FIG. 2 in accordance with embodiments of the present disclosure. The computing device 600 may include, by way of non-limiting examples, server computers, desktop computers, laptop computers, notebook computers, sub-notebook computers, netbook computers, netpad computers, set-top computers, handheld computers, Internet appliances, mobile smartphones, tablet computers, personal digital assistants, video game consoles, embedded computers, and autonomous vehicles. Those of skill in the art will recognize that many smartphones are suitable for use in the system described herein. Suitable tablet computers include those with booklet, slate, and convertible configurations, known to those of skill in the art.

In some embodiments, the computing device 600 includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

In some embodiments, the computing device 600 may include a storage 610. The storage 610 is one or more physical apparatus used to store data or programs on a temporary or permanent basis. In some embodiments, the storage 610 may be volatile memory and requires power to maintain stored information. In some embodiments, the storage 610 may be non-volatile memory and retains stored information when the computing device 600 is not powered. In some embodiments, the non-volatile memory includes flash memory. In some embodiments, the non-volatile memory includes dynamic random-access memory (DRAM). In some embodiments, the non-volatile memory includes ferroelectric random-access memory (FRAM). In some embodiments, the non-volatile memory includes phase-change random access memory (PRAM). In some embodiments, the storage 610 includes, by way of non-limiting examples, CD-ROMs, DVDs, flash memory devices, magnetic disk drives, magnetic tapes drives, optical disk drives, and cloud computing-based storage. In some embodiments, the storage 610 may be a combination of devices such as those disclosed herein.

The computing device 600 further includes a processor 630, an extension 640, a display 650, an input device 660, and a network card 670. The processor 630 is a brain to the computing device 600. The processor 630 executes instructions which implement tasks or functions of programs. When a user executes a program, the processor 630 reads the program stored in the storage 610, loads the program on the RAM, and executes instructions prescribed by the program.

The processor 630 may include a microprocessor, central processing unit (CPU), application specific integrated circuit (ASIC), arithmetic coprocessor, graphic processor, or image processor, each of which is electronic circuitry within a computer that carries out instructions of a computer program by performing the basic arithmetic, logical, control and input/output (I/O) operations specified by the instructions.

In embodiments, the extension 640 may include several ports, such as one or more universal serial buses (USBs), IEEE 1394 ports, parallel ports, and/or expansion slots such as peripheral component interconnect (PCI) and PCI express (PCIe). The extension 640 is not limited to the list but may include other slots or ports that can be used for appropriate purposes. The extension 640 may be used to install hardware or add additional functionalities to a computer that may facilitate the purposes of the computer. For example, a USB port can be used for adding additional storage to the computer and/or an IEEE 1394 may be used for receiving moving/still image data.

In some embodiments, the display 650 may be a cathode ray tube (CRT), a liquid crystal display (LCD), or light emitting diode (LED). In some embodiments, the display 650 may be a thin film transistor liquid crystal display (TFT-LCD). In some embodiments, the display 650 may be an organic light emitting diode (OLED) display. In various some embodiments, the OLED display is a passive-matrix OLED (PMOLED) or active-matrix OLED (AMOLED) display. In some embodiments, the display 650 may be a plasma display. In some embodiments, the display 650 may be a video projector. In some embodiments, the display may be interactive (e.g., having a touch screen or a sensor such as a camera, a 3D sensor, virtual/augmented reality glasses, etc.) that can detect user interactions/gestures/responses and the like.

In still some embodiments, the display 650 is a combination of devices such as those disclosed herein.

A user may input and/or modify data via the input device 660 that may include a keyboard, a mouse, virtual/augmented reality glasses sensing a position of eyes, an audio sensor sensing voice inputs, position sensor detecting positions or gestures of a body/limb, or any other device with which the use may input data. The display 650 displays data on a screen of the display 650. The display 650 may be a touch screen so that the display 650 can be used as an input device.

The network card 670 is used to communicate with other computing devices, wirelessly or via a wired connection. Through the network card 670, the autonomous vehicle may receive, modify, and/or update data from and to a managing server.

The embodiments disclosed herein are examples of the disclosure and may be embodied in various forms. For instance, although certain embodiments herein are described as separate embodiments, each of the embodiments herein may be combined with one or more of the other embodiments herein. Specific structural and functional details disclosed herein are not to be interpreted as limiting, but as a basis for the claims and as a representative basis for teaching one skilled in the art to variously employ the present disclosure in virtually any appropriately detailed structure. Like reference numerals may refer to similar or identical elements throughout the description of the figures.

Any of the herein described methods, programs, algorithms or codes may be converted to, or expressed in, a programming language or computer program. The terms "programming language" and "computer program," as used herein, each include any language used to specify instructions to a computer, and include (but is not limited to) the following languages and their derivatives: Assembler, Basic, Batch files, BCPL, C, C+, C++, C#, Delphi, Fortran, Java, JavaScript, machine code, operating system command languages, Pascal, Perl, PL1, scripting languages, Visual Basic, meta-languages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A system for determining proximity of a surgical instrument with respect to an anatomical structure, the system comprising:
    a surgical instrument configured to perform a laparoscopic surgical operation;
    an electromagnetic sensor operably coupled to the surgical instrument and configured to sense an electromagnetic wave corresponding to a position of a distal end portion of the surgical instrument within an electromagnetic field; and
    a processor configured to:
        cause a display device to display a first graphical representation of a patient, the first graphical representation including a representation of a target anatomical structure, a representation of a non-target anatomical structure, and a representation of the distal end portion of the surgical instrument;
        determine a position of the representation of the distal end portion of the surgical instrument within the first graphical representation of the patient based on the position of the distal end portion of the surgical instrument within the electromagnetic field;
        determine a proximity of the distal end portion of the surgical instrument to the non-target anatomical structure of the patient based on the determined position of the representation of the distal end portion of the surgical instrument within the first graphical representation of the patient and a position of the representation of the non-target anatomical structure within the first graphical representation of the patient;
        generate a warning based on the determined proximity; and
        cause the display device to display a second graphical representation of the patient, the second graphical representation including the representation of the distal end portion of the surgical instrument displayed relative to the representation of the non-target anatomical structure based on the determined proximity.

2. The system according to claim 1, further comprising a location sensor configured to emit a probing signal to the non-target anatomical structure and to receive a signal reflected from the non-target anatomical structure.

3. The system according to claim 2, wherein the proximity of the distal end portion the non-target anatomical structure is also based on the received signal.

4. The system according to claim 1, further comprising a laparoscopic camera configured to capture an image of the surgical instrument and the non-target anatomical structure.

5. The system according to claim 4, wherein the proximity of the distal end portion of the surgical instrument to the non-target anatomical structure is also based on the captured image.

6. The system according to claim 4, wherein the processor is further configured to perform image processing on the captured image to determine the proximity of the distal end portion of the surgical instrument to the non-target anatomical structure.

7. The system according to claim 6, wherein the processor determines the proximity based on a distance between the distal end portion in the captured image and the non-target anatomical structure in the captured image.

8. The system according to claim 1, wherein the first graphical representation is a three-dimensional model or a live video.

9. A method for determining proximity of a surgical instrument with respect to an anatomical structure, the method comprising:
    providing a first graphical representation of a patient, the first graphical representation including a representation of a target anatomical structure, a representation of a non-target anatomical structure, and a representation of a distal end portion of a surgical instrument;
    sensing an electromagnetic wave corresponding to a position of the distal end portion of the surgical instrument within an electromagnetic field using an electromagnetic sensor;
    determining a position of the representation of the distal end portion of the surgical instrument within the first graphical representation of the patient based on the position of the distal end portion of the surgical instrument within the electromagnetic field;
    determining a proximity of the distal end portion of the surgical instrument to the non-target anatomical structure of the patient based on the determined position of the representation of the distal end portion of the surgical instrument within the first graphical representation of the patient and a position of the representation of the non-target anatomical structure within the first graphical representation of the patient;
    generating a warning based on the determined proximity; and
    providing a second graphical representation of the patient, the second graphical representation including the representation of the distal end portion of the surgical instrument displayed relative to the representation of the non-target anatomical structure based on the determined proximity.

10. The method according to claim 9, further comprising:
    emitting a probing signal to the non-target anatomical structure; and
    receiving a signal reflected from the non-target anatomical structure.

11. The method according to claim 10, wherein the proximity of the distal end portion of the surgical instrument to the non-target anatomical structure is also based on the received signal.

12. The method according to claim 9, further comprising:
    capturing an image of the surgical instrument and the non-target anatomical structure.

13. The method according to claim 12, wherein the proximity of the distal end portion of the surgical instrument to the non-target anatomical structure is also based on the captured image.

14. The method according to claim 12, further comprising:
performing image processing on the captured image to determine the proximity of the distal end portion to the non-target anatomical structure.

15. The method according to claim 14, wherein the proximity is determined based on a distance between the distal end portion and the non-target anatomical structure in the captured image.

16. The method according to claim 9, wherein the first graphical representation is a three-dimensional model or a live video.

17. A nontransitory computer-readable storage medium storing a program for causing a computer to execute a method for determining proximity of a surgical instrument with respect to an anatomical structure, the method comprising:
providing a first graphical representation of a patient, the first graphical representation including a representation of a target anatomical structure, a representation of a non-target anatomical structure, and a representation of a distal end portion of a surgical instrument;
sensing an electromagnetic wave corresponding to a position of the distal end portion of the surgical instrument within an electromagnetic field using an electromagnetic sensor;
determining a position of the representation of the distal end portion of the surgical instrument within the first graphical representation of the patient based on the position of the distal end portion of the surgical instrument within the electromagnetic field;
determining a proximity of the distal end portion of the surgical instrument to the non-target anatomical structure of the patient based on the determined position of the representation of the distal end portion of the surgical instrument within the first graphical representation of the patient and a position of the representation of the non-target anatomical structure within the first graphical representation of the patient;
generating a warning based on the determined proximity; and
providing a second graphical representation of the patient, the second graphical representation including the representation of the distal end portion of the surgical instrument displayed relative to the representation of the non-target anatomical structure based on the determined proximity.

* * * * *